US006242463B1

(12) United States Patent
Reitberg

(10) Patent No.: US 6,242,463 B1
(45) Date of Patent: Jun. 5, 2001

(54) METHOD AND KIT FOR TREATING ILLNESSES

(75) Inventor: Donald P. Reitberg, Bedminster, NJ (US)

(73) Assignee: Opt-e-scrip, Inc., Morristown, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/331,913

(22) Filed: Oct. 31, 1994

(51) Int. Cl.[7] .......................... A01N 43/40; A01K 33/02; A01K 33/135

(52) U.S. Cl. ..................... 514/317; 514/654; 514/652

(58) Field of Search ................................ 514/317, 654, 514/652

(56) References Cited

FOREIGN PATENT DOCUMENTS 459387   4/1991   (EP) .

OTHER PUBLICATIONS

Sheather–Reid, R. et al., "Efficacy of Analgesics in Chronic Pain: A Series of N–of–1 Studies", *Journal of Pain and Symptom Management*, vol. 15, No.4, 1988; pp. 244–252.

Jaeschke, R. et al., Clinical Usefulness of Amitriptyline in Fibromyalgia: Results of 23 N–of–1 Randomized Controlled Trials, *The Journal of Rheumatology*, vol. 18, No. 3, 1991; pp. 447–451.

Patel, A. et al., "Clinical Usefulness of n–of–1 Randomized Controlled Trials in Patients with Nonreversible Chronic Airflow Limitation", *Am Rev Respir Dis*, 1991; 144:962–964.

Balestra, D. et al., "Ulcerative Colitis and Steroid–Responsive, Diffuse Interstitial Lung Disease", *JAMA*, Jul. 1, 1988; vol. 260 No. 1.

Max, M.B. et al., "The Design of Analgesic Clinical Trials", *Advances in Pain Research and Therapy*, vol. 18, 1991; 178–192.

Cook, D. et al., "A Diagnostic and Therapeutic N–of–1 Randomized Trial", *Canadian Journal of Psychiatry*, vol. 38, 1993; 251–254.

Guyatt, G.H. et al., "A clinician's guide for conducting randomized trials in individual patents", *CMAJ*, vol. 139, 1988; 497–503.

Wulff, H.R., "Single Case Studies An Introduction", *Scandanavian Journ. of Gastroenterology*, 1988, vol. 23. S. 147, pp. 7–10.

Keller, J. et al., "An N of 1 Service: Applying the Scientific Method in Clinical Practice",*Scandanavian Journ. of Gastroenterology*, 1988, vol. 23. S. 147, pp. 22–29.

Guyatt, G.H. et al., "N–of–1 Randomized Trials for Investigating New Drugs", *Conrolled Clinical Trials*, 11:88–100 (1990).

Larson, E.B., "N–of–1 Clinical Trials A Technique for Improving Medical Therapeutics", *The Western Journal of Medicine*, 1990; 52–56.

Langer, C. et al, "The Single Subject Randomized Trial A Useful Clinical Tool for Assessing Therapeutic Efficacy in Pediatric Practice", *Clinical Pediatrics*, Nov. 1993; 654–657.

Guyatt, G.H., et al., "The n–of–1 Randomized Controlled Trial: Clinical Usefulness", *Annals of Internal Medicine*, 1990; 112:293–299.

Spiegelhalter, D., "Statistical Issues in Studies of Individual Response", *Scandanavian Journ. of Gastroenterology*, 1988, vol. 23. S. 147, 40–45.

Larson, E.B. et al., Randomized Clinical Trials in Single Patients During a 2–Year Period; *JAMA*, vol. 270, No. 22, 1993; 2708–2712.

Robin, E. et al., "Single Patient Randomized Clinical Trial Opiates for Intractable Dyspnea", *Chest*, 1988; 90:888–892.

Guyatt et al. (1990). N–of–1 Randomized trials—Where do we stand? Western Journal of Medicine, 152(1): 67–8.*

Johannsen et al. (1991). Combined Single Subject Trials. Scandinavian Journal of Primary Health Care 9(1): 23–7.*

Johannsen et al. (1992). Cimetidine on–demand in dyspepsia. Scandinavian Journal of Gastroenterology 27(3): 189–195.*

Spilker, Bert, "Planning Special Types of Clinical Trials: Single–Patient Clinical Trials" *Guide to Clinical Trials*, Part III, Chapter 38 pp. 277–282, 1996.

Biosis 94:537363 1994.*

\* cited by examiner

*Primary Examiner*—Gary Geist
*Assistant Examiner*—Mahreen Chaudhry
(74) *Attorney, Agent, or Firm*—Davidson, Davidson & Kappel, LLC

(57) ABSTRACT

Methods and kits for determining appropriate treatment for illnesses in humans or animals are disclosed. The method includes:

providing a test kit containing a random arrangement of drug(s) and placebo(s) and/or alternative treatment(s) along with a questionnaire or other instrument designed to elicit data concerning the safety, efficacy and desirability of a treatment;

administering the drug(s) and placebo(s) and/or alternative treatments to each member of the pool in a random, double blind fashion and following up on patient outcomes as appropriate post-study;

assembling a database from the completed pool questionnaires and revealing the random schedule to uncover drug and placebo treatment periods;

providing the same kit to a patient in need of the same treatment and comparing the results obtained from the single patient trial with those obtained from the pool to determine an optimal treatment for the patient with the drug; and administering a treatment consistent with the optimal treatment.

47 Claims, No Drawings

METHOD AND KIT FOR TREATING ILLNESSES

BACKGROUND OF THE INVENTION

The present invention relates to improving the treatment of chronic illness in humans and animals. In particular, the invention relates to kits and methods that improve chronic treatments using data obtained from individual random crossover (n=1 or single patient) double-blind studies.

Inappropriate prescribing of potent and potentially dangerous drugs is a problem of staggering dimensions. Nonetheless, no commercial solution has been advanced to ensure appropriate treatment. Presently, doctors prescribe medications which have approved indications determined by large clinical trials. Drug manufacturers also demonstrate a product's safety and effectiveness using well controlled clinical studies in populations likely to require its use (e.g. hypertensive patients for antihypertensive drugs). Relatively small numbers of highly selected subjects are utilized. Too often, these studies do not accurately predict the safety and efficacy of a medication for individuals actually treated in practice.

Thus, prescribers are at a disadvantage because a highly selected, often homogeneous group of patients is actually studied for marketing approval. The prescribing physician often cannot distinguish which drugs are safe and effective for his/her heterogeneous collection of individual patients. Even in homogeneous groups of patients, individual variation is usually large when a pharmaceutical company measures a drug's disposition and activity. Therefore, average results may be poorly suited to the needs of any given individual. It is rarely clear to the prescribing physician how an individual patient might respond to a given medication. This is because all people respond differently, both positively and negatively, based upon individual genetic and environmental factors.

Furthermore, the physician rarely has objective information to help decide between alternative therapies for an individual patient. Although the physician wants unbiased data concerning how a patient responds to a given therapy, such data is almost never available unless the patient is in a drug trial. The physician is almost always required to use subjective "clinical judgment".

Pharmaceutical manufacturers are also at a disadvantage since they have no means of providing unbiased data for individual patients. Manufacturers rarely receive feedback on how a drug is used in actual practice unless an adverse event is reported. Other organizations often need unbiased information for regulatory, patient care and business purposes. Currently, unreliable retrospective databases, such as government or health maintenance organizations' epidemiologic databases, are used.

In 1985, investigators proposed a single-patient drug trial as a possible solution. Using this study design, a patient is treated with a medication and a placebo in a double-blind randomized manner (n=1 or single patient drug trial). This approach permits assessment of whether a medication regimen is appropriate for an individual patient in terms of medical benefit and harm. This approach eliminates patient/physician bias by making the medication and placebo look and/or taste the same. Thus, a toxic or ineffective treatment can be avoided by using objective criteria and new treatment regimens can be pursued for well documented reasons and similarly tested, if needed. This alternative is purely subjective trial and error.

The single-patient method, however, has significant shortcomings. It has failed to provide validated results. There was no appreciation that the data obtained from the single trial should be compared against a database compiled from similarly affected and tested patients. Moreover, no guidance was provided concerning therapeutic alternatives based upon a database comprised of earlier patient experience during single-patient trials.

No commercial products are believed to be available which allow objective and definitive measurement of individual patient compatibility with drug treatment compared to placebo or a therapeutic alternative. The present invention addresses this need.

OBJECTS AND SUMMARY OF THE INVENTION

It is therefore an object of the present invention to develop methods and kits which can assess the appropriateness of specific drug treatment in individuals, particularly those suffering from chronic illnesses.

It is a further object to provide methods and kits for testing therapeutic alternatives for drug treatments in individuals.

Thus, in one aspect, the invention includes a method of treating human and veterinary illnesses. The method includes:
a) providing to a pool of humans or animals in need of such treatment a test kit containing:
   i) a supply of a drug indicated or proposed for the treatment of an illness;
   ii) a supply of a placebo substantially identical in appearance to the drug,
   iii) a questionnaire designed to elicit from each pool member to be treated information concerning the actual usage, safety, efficacy and desirability of the selected treatment;
b) administering the drug and placebo to each member of the pool according to a random, double-blind schedule;
c) assembling a database from the pool based on the answers provided from the individual questionnaire;
d) revealing the random schedule and comparing the data obtained from known drug and placebo treatment periods;
e) providing a test kit containing the same materials as set forth in a) to a human or animal also in need of such treatment to obtain a separate or second set of data concerning the safety, efficacy and desirability of said treatment;
f) administering the drug and placebo to the human or animal according to a random, double-blind schedule;
g) assembling the second or separate database based on the answers provided to the questionnaire;
h) revealing the random schedule to uncover drug and placebo treatment periods;
i) comparing the data obtained from the pool with that obtained from the single human trial to determine an optimal treatment of the human or animal with the drug; and
j) administering to the human or animal a treatment consistent with the optimal treatment. The new dosing regimen for optimal therapeutic effect and quality of life can also be retested, if and when deemed appropriate, by the clinician and/or patient.

The method is suitable for evaluating and validating any prescription or non-prescription treatment regimen or medication for individuals as well as demographic groups. Using this method, one can periodically obtain further outcome information on tested individuals.

Other aspects of the invention include a method and kit for determining therapeutic alternatives and verifying generic equivalence of known medications. These methods include:

a) providing to a human or animal a test kit containing:
   i) a supply of a drug indicated for the treatment of an illness;
   ii) a supply of a therapeutic alternative or generic equivalent candidate substantially identical in appearance to the drug,
   iii) a questionnaire designed to elicit from the human or animal information concerning the safety, efficacy and desirability of the treatment for the human or animal;
b) administering the drug and therapeutic alternative to the human or an animal according to a random, double-blind schedule;
c) assembling a database by eliciting from the human or animal caretaker answers to the questionnaire; and
d) revealing the random arrangement schedule to determine the relative effectiveness of the therapeutic alternatives in the human or animal by comparing the data obtained from knowing drug and alternative treatment periods.

There are several advantages associated with the present invention. For example, patients benefit by the assurance of treatment with appropriate drug and dosing regimen. The method is particularly useful before committing a patient to a long term drug treatment regimen. Documented evidence of the benefit is provided. Unnecessary side effects and expense can be avoided.

Government agencies could also benefit by the availability of a dynamic database on drug efficacy and safety in individuals. The inventive method also provides an alternative means for approving new drugs. In this aspect, the new drug or therapeutic alternative could be tested according to the methods described herein against a placebo or a known effective agent and/or indicated therapy in individuals and/or a pool of suitable candidates. This is a particular advantage to the pharmaceutical industry and affords a method to validate the therapeutic equivalence of generic drugs as well as non-generic therapeutic alternatives.

Insurers and managed care organizations could benefit by having a reliable "second opinion" to help avoid expensive, prolonged, unneeded, or toxic treatments, and promote utilization of safe and effective therapies.

The present invention provides advances over prior art single patient drug trials (n=1) by optimizing treatment for the individual. Unlike (n=1) studies, which by definition, had a sample size of one, the invention includes comparing the data obtained from the individual with a database accumulated for an entire tested population, referred to as a pool herein. This results in the opportunity to create a prospective, frequently updated epidemiological database which has value not only for regulatory approvals or post-marketing surveillance of drug safety and efficacy, but also for optimizing outcome in individuals as well.

DETAILED DESCRIPTION OF THE INVENTION

The present invention includes a method and kit for determining the appropriate treatment of an illness. The method includes:

a) providing to a pool of humans or animals in need of such treatment a test kit containing:
   i) a supply of a drug indicated for the treatment of an illness;
   ii) a supply of a placebo substantially identical in appearance to the indicated drug,
   iii) a questionnaire designed to elicit from each member of the pool information concerning the safety, efficacy and desirability of the selected treatment;
b) administering the drug and placebo to each member of the pool according to a random, double-blind schedule;
c) assembling a database by eliciting from the pool data from the answers to the questionnaire;
d) revealing the random schedule to uncover drug and placebo treatment periods;
e) providing a test kit containing the same materials as set forth in a) to a human or animal also in need of such treatment to obtain a second or separate set of data concerning the safety, efficacy and desirability of the treatment;
f) administering the drug and placebo to the human or animal according to a random, double-blind schedule;
g) assembling a separate database by eliciting from the human or animal caretaker answers to the questionnaire;
h) revealing the random schedule and comparing the data obtained as a result of known active(s) and placebo(s) treatment periods;
i) comparing the results obtained from the first set of data obtained from the pool with the second set of data obtained from the single trial to determine an optimal treatment of the human or animal with the drug; and
j) administering to the human or animal a treatment consistent with the optimal treatment, based upon individual and group outcome. Results from the individual, and post-study follow-up data can also be added to the general database.

Even after the data obtained from the questionnaires is obtained, the caregiver can continue to periodically use the same kit or other kits with different test articles, analyzing the further results for relative scoring, or monitoring further treatment based on physician and patient awareness of study results.

For purposes of description of the present invention, certain terms are described below. Generally, however, the terms have the commonly understood meaning known to those of ordinary skill in the art.

Drug shall mean a medicament, biologically active ingredient, or pharmaceutical dosage form containing an active ingredient effective for one or more medical conditions. The drug may be in any known dosage form including tablets, capsules, solutions, elixirs, ointments, creams, etc.

Placebo shall mean an inert or inactive dosage form having an appearance and/or other organoleptic/sensory characteristics substantially identical to an active drug.

Treatment or treating includes administering a generally recognized effective amount of a drug for the purpose of alleviating or curing a disease or deficiency.

Optimal or optimizing treatment means a treatment regimen which has been adjusted or validated in view of a comparison of objective data relating to one or more treatment periods with one or more active medicament(s) and one or more of placebo, therapeutic alternative or generic equivalent. This is further adjusted by consideration of outcomes from similarly tested populations. Treatments consistent with optimal treatment are those which adjust the time, manner or amount of a drug or therapy for maximum effect, or even cease to treat with the drug or therapy.

Supply means a quantity sufficient for completing a statistically valid evaluation of a treatment method in an individual.

Therapeutic alternative means a medicament having a non-identical chemical composition from a known medicament but achieves substantially the same bio-effect in an individual.

A generic drug or medicament means a substantially identical active ingredient to a known composition.

Chronic shall mean treatment for a condition which lasts an indefinite period of time. Treatments amounting to more than a single course of therapy. Maintenance dosing regimens are also contemplated.

Prolonged therapy shall mean therapy wherein doses are administered to a patient over a period of greater than 10 days, including multiple episodes or recurrences of shorter duration. For example, a psoriasis or herpes episode may require treatments of less than 10 days but the condition requires prolonged therapy.

The term "double-blind" shall be consistent with its known meaning and include known techniques such as single or multiple crossover techniques well known to those of ordinary skill. Double-blind means that the patient, or caretaker if appropriate, and care-giver do not know exactly when the drug, alternative or placebo is given.

For purposes of description, the method and kit can be described as a Single-Patient Assessment System (SPAS). The SPAS provides a health care practitioner with objective data based on each individual patient's unique circumstances, allowing therapy to be tailored to individual needs. In addition, the unique method generates prospective, directly measured epidemiologic safety and efficacy data. Pharmaceutical companies can use this data to gain regulatory approval for new indications or to differentiate efficacy and/or safety benefits between competing products, and to provide pharmaceutical manufacturers, government and health care organizations with demographic and usage data on products. Importantly, the database can also be used by government agencies to monitor the safety and efficacy of drugs in the marketplace. Using statistical sub-group analyses, data can be generated to define the level of efficacy or safety in various special populations. For example, data can be segregated by age, disease severity, onset of illness, and concurrent medications.

One preferred embodiment of the invention includes the use of the SPAS to demonstrate the effectiveness of the specific treatment for the specific individual, that is, to document the probability that the medication is beneficial without causing unacceptable side effects. Specifically, the system consists of a clinical evaluation kit which generates definitive guidance regarding the safety and efficacy of drug therapy in each individual patient. The kit contains a full supply of medication to be evaluated and/or placebo, as well as all instructions and evaluation instruments for professionals and patients.

A key feature of the present invention is the double-blind manner in which the drug or placebo, or alternative, is being administered. Both the patient and the physician are unaware of what any dose given is. This is essential since placebo and active drug are randomly administered and look identical to eliminate any bias in the results. A neutral observer/administrator keeps the record of the random arrangement, assembles the data from completed questionnaires and after completion of the test, "breaks the code" to reveal the schedule of drug and/or placebo doses and analyze the accumulated data. The physician and/or patient is/are then given a report on the efficacy and safety of the drug in question. The report has the feature of being validated because the data obtained from the single patient is compared to data obtained from a pool of individuals who also required treatment, were given the kit, and were followed up when appropriate for efficacy and safety data post-testing. This can be used for guidance in directing further therapy, referred to herein as a treatment consistent with optimal treatment. The results of individual assessments can be monitored, with subsequent outcomes added to the database. Data generated from a pool of individual studies can then form the basis of a large population database reporting system which serves to further validate the effectiveness of any singular trial or single indication for a medication.

The SPAS includes means for providing the drug(s), placebo(s) and questionnaire(s) such as a kit. The kit may contain convenient pocket-sized cards which contain a sufficient supply of active drug(s) and placebo(s) or therapeutic alternative(s) in blister packages labeled with the day and time of dosing. For example, a kit may contain eight cards for a required trial, each corresponding to one of eight weeks of treatment, and contain daily regimens of either active drug or placebo, at carefully selected times during the eight week period. The tablets in the card are "blinded" so that neither the patient nor the physician is aware of which preparation is received at any given time. In an emergency, the random arrangement can be broken. Under normal circumstances, the code will not be made available, thereby eliminating any bias in the results.

At various times during the evaluation, the program prompts the clinician, patient and/or guardian/observer to fill out questionnaires or other instruments which assess numerous efficacy and safety variables relating to improvements in physical and behavioral symptoms.

At the end of the study, all drug cards (used and unused) as well as questionnaires are returned and the results are evaluated. These results are provided to the physician and patient so that guidance can be provided regarding the safety and efficacy of the treatment for the tested patient. These data can also be added to a master database along with other data on family history, demographics, socioeconomic factors, and post-study outcome.

Numerous drugs and indications can be evaluated using the methods of the present invention. Suitable illness for which the present invention can be used include, without limitation, asthma, cancer, epilepsy, schizophrenia, minimal brain dysfunction, mania, depression, anxiety, hypertension, angina, congestive heart failure, cardiac arrhythmias, pain, etc.

Suitable drugs for evaluation include, without limitation, those agents currently approved for the above-identified conditions as well as agents awaiting approval and new chemical entities. For example, the drug can be selected from anti-asthmatic agents, dental agents; anti-epileptic agents, anti-psychotic agents, anti-depressants, cardiovascular agents, respiratory agents, antihypertensive agents, diabetic agents, steroidal and non-steroidal anti-inflammatory agents, opiates, narcotic and non-narcotic analgesics, hematologic agents, musculoskeletal agents, anti-anxiety agents, gastro-intestinal agents, dermatologic agents, and anti-allergy medications. Other categories not specifically mentioned are intended as well. Particular agents well suited for the methods of the present invention include methylphenidate, estrogen-containing agents, anti-asthmatic agents, cardioactive agents, and antidepressant agents.

Oral, mucous membrane, nasal, surgical, musculoskeletal, central nervous system, urinary tract, psychiatry, nephrology, neurology, genital, podiatry, chiropractic, pediatric, geriatric, acupuncture, allopathy, homeopathy and osteopathy treatments can be also be evaluated.

It is to be understood that where veterinary treatments and therapies are to be tested, the questionnaires and assembly of data are provided by human caretaker/observers. Furthermore, it is to be understood that the term questionnaire refers generally to a means by which information can be related back to the evaluator. The results need not be transmitted in written form. Computer-assisted data recording and communication devices and measuring instruments can also be part of the database assembly step.

An additional list of uses includes:

1) Socially/medically controversial uses for drugs where the relationship of risk to benefit is not well defined. For example, depression, asthma, and hyperkinetic behavior are representative chronic ailments which can be evaluated and available treatments can be challenged.

2) Chronic disease states which may or may not benefit from long term drug treatment. Controlled drug "holidays" are needed to test if chronic medication is paradoxically compromising quality-of-life, has no effect or is helping and should be continued. Category examples include cardiovascular disease, hypertension, and arthritis.

3) "Compassionate" Investigational New Drug Application (IND) drug trials for drugs/indications which command a fast track regulatory approval process, such as drugs used for treatment of AIDS. Pharmaceutical companies can pursue early "compassionate" marketing in the form of a drug trial in subjects who urgently need the new therapy. Also, early New Drug Application (NDA) approval can be pursued by carefully controlling drug use, investigational documentation and data analysis in the community-practice setting. These regulatory strategies can be economically and effectively accomplished using Single-Patient Assessment Systems (SPAS).

4) Clinical comparison between innovator and generic drugs. Single-Patient Assessment Systems (SPAS) can be used to validate or invalidate use of generic drugs for regulatory or marketing purposes. Single-Patient Assessment Systems (SPAS) can be used to gain approval for generic drugs which are not readily approved by traditional bioequivalence testing. The method and kit can offer a consumer assurance of a successful switch from the innovator's product, and assurance that the drug actually improves his or her quality-of-life.

Another example of the method and kit is for evaluation of new or generic drugs, or evaluating new indications for marketed drugs or therapeutic equivalents. This includes determining a therapeutic alternative for a known drug for an individual requiring treatment. This aspect includes:

a) providing a human or animal a test kit containing:
   i) a supply of a drug indicated for the treatment of an illness;
   ii) a supply of a therapeutic alternative substantially identical in appearance to said drug,
   iii) a questionnaire designed to elicit from the person or animal caretaker information concerning the safety, efficacy and desirability of the treatment;
b) administering the drug and therapeutic alternative to the person or animal according to a random, double-blind schedule;
c) assembling a database from the answers to the questionnaire; and
d) revealing the random arrangement schedule to determine the effectiveness of the therapeutic alternative by comparing the results obtained from known drug and alternative treatment periods.

This method may also include additional steps which serve to validate the data obtained in any single trial. The steps are:

e) providing the same type of test kit to a pool of humans or animals in need of such treatment and obtaining from the pool a second set of data including post-study following information where appropriate, concerning the safety, efficacy and desirability of the treatment with the drug and therapeutic alternative; and
f) comparing the data obtained from an individual with that obtained from the pool to verify the effectiveness of the therapeutic alternative.

The method described herein also contemplates that the therapeutic alternative is a generic equivalent for the drug and/or the same drug but at a different dosage or even same dosage.

The present invention has a myriad of uses. For example, it can be used to test, confirm or verify a particular therapy's safety and efficacy. It can also provide demographic, marketing, sales or professional usage information. New indications, patterns of use, compliance, therapy relationships to other disease states, relationships between concomitant medications, laboratory result relationships can be uncovered. The kit can be used in regulatory filings, dose titration, placebo controlled, crossover, food effect, dose proportionality, bioavailability, single dose, multiple dose and market research studies. Age effects, socioeconomic effects, sex effects, and disease effects can also be determined. Moreover, the role of heredity, diet, geographic location, demographics, occupation, epidemiology, patient education, drug interactions, dose response, time to onset, dosage individualization, regimen individualization, dose finding, dose ranging, rising dose, dose titration or overdose can be determined.

The kits of the present invention also have value to physicians. Legal documentation concerning rational drug therapy, compliance, monitoring, documentation of decision making, appropriateness of therapy, ease of following instructions for administration of therapy and documentation of safety and efficacy are all achieved by the inventive process. The method gives a reason for patient compliance and drug effects, a mechanism for follow-up of therapy, the ability to ease concerns about safety-efficacy. The ability to use blinded placebo treatment methods and the ability to remove bias from decision making, ease of screening out psychosomatic illness are all provided. The kit can provide drug holidays in blinded manner to foster compliance, make available objective feedback and an unbiased and rational approach to therapy. The kit allows the involvement of all physicians and/or patients in clinical trials, early patient participation in therapy, decreases time for regulatory submissions with less initial use of specialists in clinical trials and less dependence on traditional clinical investigators. All of these features decrease overall medical costs, the costs of new drug development, increases accuracy of diagnoses and potentially decreases malpractice.

The kit and method has value to patients by lessening the fear of inappropriate medicine and providing the feeling that something important is being done. Individualization of therapy for patient, decreased side effects, increased efficacy, decreased risk of treatment, controlled drug holidays are all realized. Patients have the enhanced ability to use new and unapproved treatments when needed with the enhanced ability to participate in clinical trials. The kit decreases overall costs of treatment, eliminates unnecessary therapies and tests, reminds patients when to use drugs, prevents under or overdoses, fosters relationships with clinicians, increases understanding of disease and drug.

Industry will benefit from the invention by having a means to gain early drug approval, a marketing tool, a reduction of clinical trial costs, better clinical trials, larger clinical trial database, broader patient population for clinical trials, ability to conduct well controlled, small scale, initial clinical trials, a means for post-marketing surveillance, as well as a means to document therapeutic bioequivalence.

The kit and method's value to government is realized by providing a means to remove clinician/company/patient bias in important therapy, protecting the public from inappropriate drug use, decreasing the cost of public health, and lowering the cost of effective clinical assessment of new and existing drugs, more rapidly approving new drugs and indications, providing highly controlled methods to deploy needed but unapproved treatments, and providing new methods for phase I through IV treatment evaluations.

Third party healthcare organizations, insurers and managed care organizations benefit by the assurance of need for expensive and/or potentially dangerous therapies, overall decreased cost of treatment, decreased use of unneeded and/or multiple therapies.

Pharmacists benefit by the availability of new products, enhanced role in patient care, greater interaction with patients and with other health care professionals.

EXAMPLES

The following non-limiting examples serve to provide further appreciation of the invention but are not meant to restrict the effective scope of the invention.

Example 1

In this example, the usefulness of methylphenidate (Ritalin) treatment in a hyperactive child (Minimum Brain Dysfunction) is evaluated.

Rationale: Use of a stimulant in children is highly controversial and widely publicized/perceived as a problem. Parents demand a clear-cut reason to use addictive and often poorly tolerated medication.

Technology: Consists of instructions, "calendar" packaging for drug and a substantially identical looking placebo to assure appropriate dosing and monitor compliance, questionnaire assessment forms and instructions. Completed forms are sent to a neutral observer who has assigned the random, multiple crossover schedule of drug and placebo periods. Only the observer has access to when active drug and placebo were taken and analyzes the data. Results are mailed to the physician and, in this case, parent for use in evaluating the usefulness of the therapy. The physician and parent are contacted, e.g., every three months to provide data on therapies utilized, and perceived outcome, until the condition resolves. The data is also added to a post-marketing surveillance database for use in evaluating future individual study results, and for access by drug companies, regulatory agencies, and health care organizations.

The questionnaire portion of the kit includes an initial consent form for the parent or guardian to complete. The questionnaire also provides background information on the study and possible side effects associated with the medication. Also included therein is a portion for providing relevant patient and family histories. More importantly, the questionnaire, in this case includes a portion for the weekly input by parents or guardian and school observers of answers to questions relating to the drug evaluation. Typical questionnaire sheet for these portions are shown below as Table 1 and Table 2. Physician questionnaires are similarly arranged.

TABLE 1

Safety Net Systems, Inc.     Hyperactive Child Drug Evaluation Kit WEEK 1

PARENT QUESTIONNAIRE

Kit Identification Number _____ Date Information Recorded ___/ ___/ ___
                                                                                                    mo    day    yr Child's name _____ Parent/Guardian Name _____

DEGREE OF ACTIVITY
Place an X on line where appropriate.

| OBSERVATION | NOT AT ALL | VERY MUCH |
|---|---|---|
| Restless or overactive, constantly talking, sudden movements (tics), trouble sleeping | | |
| Excitable, impulsive | _____ | |
| Disturbs others, fights | _____ | |
| Fails to finish things, short attention span, daydreams, won't watch TV for long | | |
| Constantly fidgeting, can't sit still | _____ | |
| Inattentive, easily distracted | _____ | |
| Demands must be met immediately, easily frustrated, unnecessarily seeks help | _____ | |
| Cries often and easily, sad, fearful, | _____ | |

TABLE 1-continued

Safety Net Systems, Inc.  Hyperactive Child Drug Evaluation Kit
WEEK 1
PARENT QUESTIONNAIRE
Kit Identification Number _____  Date Information Recorded ___/___/___
mo  day  yr
Child's name _____  Parent/Guardian Name _____

DEGREE OF ACTIVITY
Place an X on line where appropriate.

| OBSERVATION | NOT AT ALL | VERY MUCH |
|---|---|---|
| threatens suicide, overly sensitive, easily hurt, anxious to please, afraid of the dark, has nightmares | | |
| Mood changes quickly and drastically | | |
| Temper outbursts, explosive and unpredictable | | |
| Poor group participation, socially inadequate, isolated, not affectionate, bullies others, lacks friends, steals, lies, truancy, runs away from home, destructive, cruel to animals, trouble with police | | |
| Defiant, uncooperative, does not recognize authority, talks back, refuses to obey, fails to return home on time | | |
| Abnormal development-clumsiness, speech problems, sexual problems, abnormal eating habits | | |

To be completed by parent at the end of each study week.

TABLE 2

Safety Net Systems, Inc.  Hyperactive Child Drug Evaluation Kit
WEEK 5
SCHOOL QUESTIONNAIRE
Kit Identification Number _____  Date Information Recorded ___/___/___
mo  day  yr
Child's name _____  School Observer Name _____

DEGREE OF ACTIVITY
Place an X on line where appropriate.

| OBSERVATION | NOT AT ALL | VERY MUCH |
|---|---|---|
| Restless or overactive, leaves seat unexcused, nervous, tense | | |
| Excitable, impulsive | | |
| Disturbs other children, fights, noisy, tapping, humming | | |
| Fails to finish things, short attention span | | |
| Constantly fidgeting | | |
| Inattentive, easily distracted | | |
| Demands must be met immediately, easily frustrated, speaks out of turn | | |
| Cries often and easily, sad, sullen, overly sensitive, easily hurt, anxious to please | | |
| Mood changes quickly and drastically | | |

TABLE 2-continued

Safety Net Systems, Inc.     Hyperactive Child Drug Evaluation Kit
WEEK 5
SCHOOL QUESTIONNAIRE Kit Identification Number _____ Date Information Recorded \_\_\_/\_\_\_\_\_/\_\_\_ mo    day    yr

Child's name _____ School Observer Name _____

DEGREE OF ACTIVITY
Place an X on line where appropriate.

| OBSERVATION | NOT AT ALL | VERY MUCH |
|---|---|---|
| Temper outbursts, explosive and unpredictable | | |
| Poor group participation, socially inadequate, isolated | | |
| Defiant, uncooperative, does not recognize authority | | |
| Abnormal development-bedwetting, clumsiness, speech problems, sexual problems, abnormal eating habits | | |

To be completed by school observer at the end of each study week.

As a result of undergoing the study, all interested parties have a clear understanding of the value of the medication for this particular patient.

Example 2

In this example, the kit described in Example 1 is used to again evaluate the usefulness of methylphenidate (Ritalin) treatment in a hyperactive child except that all interested parties have the benefit of a set of data generated from a pool of patients having a similar need for treatment. The trial calls for 40 mg daily given at 10 mg four times daily compared to identical appearing placebo given four times daily. After completing the trial and questionnaire, the processed data provides the following results which are statistically determined:

the patient's attention span is observed to have improved substantially during the periods in the trial when the methylphenidate is being given;

temper outbursts are observed to increase slightly during placebo periods;

sleep patterns are observed to be statistically altered during methylphenidate periods; and teacher comments corroborate improved attention span during methylphenidate dosing periods.

All results obtained from the data are then compared against the results provided by data amassed from a pool of about 200 patients with the same disorder. Of these 200 patients, 55 experienced encouraging results (as did the current patient) and were continued on 40 mg daily treatment. Of these 55 patients, 5 were lost to follow-up, with 50 remaining for prospective evaluation. Because the physician would now choose to continue the patient on 40 mg methylphenidate daily based solely on the isolated SPAS single patient drug trial results, he now takes the opportunity of reviewing the pooled data on the 50 patients. This is done to understand under what circumstances this individual patient would likely continue to show benefit from methylphenidate 40 mg treatment, and what conditions lead to treatment failure.

The pool of 50 patients who continued treatment had the following scores following the original SPAS testing:

| | |
|---|---|
| Attention Span | 100% had substantial improvement |
| Sleep Patterns | 50% were statistically altered |
| | 50% were not statistically altered |
| Teacher Comments | 80% corroborate improved attention span |
| | 20% did not corroborate improved attention span |

All 50 patients were followed up by telephone interview monthly for nine months or more, and outcomes were prospectively documented. It was found that all patients who had no statistically altered sleep disturbances on the original SPAS test continued to be well maintained on treatment. However, within two months, all patients who had statistically altered sleep patterns on SPAS testing showed loss of symptom control, and in 90% severe episodes of bizarre behaviors were reported; two of these patents experienced a grand mal seizure. All patients who had a statistically altered sleep disturbance had to be discontinued from treatment within two months.

Despite the initial, generally positive result of the SPAS single patient drug trial, the prescribing physician has a strong, objective basis for not continuing treatment with methylphenidate 40 mg daily because the pooled data from similar patients clearly indicate that continued treatment in the presence of sleep alteration is at great risk (90% chance of a severe adverse event) with limited potential benefit. The continuing validation process using pooled data, which is a subject of this invention, provides additional data which is essential to formulating a rational therapeutic decision.

The physician may now decide to use a different pharmacologic intervention in a chemical class which is not as frequently associated with sleep disturbance (e.g., amitriptyline), or may decide to use non-pharmacologic treatments, such a behavioral therapy. The amitriptyline dose selected may be tested using another SPAs designed for that drug, and the process continued until the patient is on a documented safe and effective drug regimen.

Example 3

Test kit:

Antihistamine for house dust induced allergic nasal congestion.

A clinician writes a prescription for a test kit which has been extensively tested in patients similar to his. The product labeling available to the clinician advises him that it has been used in 2,000 patients with house dust allergic nasal congestion to date. The antihistamine was found to be clinically useful with a modest side effect profile in 1500 patients, 250 experienced untoward drowsiness and 250 experienced no clinical benefit. The test was completed and useful only in subjects with an 8th grade educational level or higher who report at least moderate symptoms on study initiation. Subjects with mild symptoms often failed to complete the study. The clinician recognizes that his patient is college educated with severe symptoms and writes the prescription, confident that he has a good candidate for the test.

Example 4

The pharmaceutical company marketing an antihistamine submits a 2,000 patient database to the government for approval of a new claim for the product: house dust allergic nasal congestion. The company agreed with a request from the government agency that, as a condition for expedited review and acceptance, continuous post-marketing surveillance will be conducted for this indication by marketing the product in a SPAS test kit. This testing of each subject on initiation of therapy will continuously ensure that each patient is evaluated for appropriateness of treatment prior to commitment to a chronic regimen. In addition, it allows the company to provide a monthly update to the government of drug efficacy and safety in the entire population using the product for house dust allergic nasal congestion. Physician and patient labeling can be revised if necessary. Also, it is now found that the product has more side effects if the patient is also taking cimetidine. Therefore, the company can now advise the government agency of a possible drug interaction, and warn clinicians of a possible drug interaction in the product labeling.

Example 5

In this example, the validity of using a sustained release formulation of verapamil 240 mg once daily as a therapeutic alternative to sustained release propranolol 180 mg once daily in a hypertensive 45 year old male is shown. The trial during which the two medications are randomly administered in a double-blind manner is six weeks. The questionnaire used is set up in a manner similar to that described in above examples except that the questions elicit information related to the disease of hypertension. Blood pressure is taken daily by the patient and weekly by the physician. Lab values and vision tests are also reported weekly by the physician. At the end of the trial period it is determined that mean systolic blood pressure increases 3% and mean diastolic pressure is essentially stable. Both values are statistically insignificant and the therapeutic alternative selection is objectively validated.

Example 6

In this example, the data accumulated for example 5 is compared against that acquired from a pool of 100 male patients who were switched from beta blockers, including propranolol, to calcium channel blockers, including verapamil. The results of example 5 are found to be in agreement with those found from the pool. On this basis, a health maintenance group can objectively eliminate the use of beta blockers for males fitting the pool profile with hypertension under its care.

Example 7

In this example, each member of a pool of fifty patients is given a test kit containing a four week supply of an antihistamine and a four week supply of a look-alike placebo arranged in a multiple-crossover, random order along with a questionnaire designed to confirm the appropriateness of the therapy. After all of the kits have been finished and individual results provided to the patients and care-givers, the pooled data supplied from the questionnaire is evaluated. It is found that a question (number 12) relating to the secondary side-effect of dry mouth for the drug was poorly understood by the pool members and failed to provide a statistically significant result for the database. Moreover, several patients reported heart palpitations and related cardiac disturbances. Thus, question number 12 is dropped from the questionnaire and replaced with one tested and validated for comprehension at the 5th grade education level; also a new question relating specifically to cardiac symptoms is added. All further kits for the antihistamine trials are made to contain the revised, validated questionnaire.

A clinician writes a prescription for a test kit containing the revised questionnaire and antihistamine/placebo combination for a patient. The patient completes the course of therapy as directed over the eight week course and completes the weekly questionnaire relating to the trial and mails them to a neutral observer who also has the key to the random arrangement of drug/placebo. At the end of the trial, a statistical analysis of the trial is provided to the clinician who evaluates the results in view of the data provided by the pool of patients. The clinician thus has an objective basis for continuing the therapy since this individual was found to have substantially improved symptoms, and members of the tested pool with similar results were found to do well with continued treatment at three and six months.

As will be readily appreciated, numerous variations and combinations of the features set forth above can be utilized without departing from the present invention as set forth in the claims. Such variations are not regarded as a departure from the spirit and scope of the invention, and all such modifications are intended to be included within the scope of the following claims.

What is claimed is:

1. A method of evaluating the therapeutic response of individual human patients to chronic therapy with a drug, comprising:

a) assembling from a plurality of crossover single patient drug trials a patient population database of information concerning the safety, efficacy and desirability of a drug administered according to a randomized, double-blind schedule with a placebo, said drug being selected from the group consisting of a drug for treating hyperkinetic behavior, an anti-depressant drug, an anti-anxiety drug, an anti-asthmatic drug, an anti-epileptic drug, an anti-psychotic drug, a cardiovascular drug, a respiratory drug, an antihypertensive drug, an anti-diabetic drug, a steroidal anti-inflammatory drug, a non-steroidal anti-inflammatory drug, an opioid analgesic, a non-narcotic analgesic drug, an anti-cancer drug, a hematologic drug, a musculoskeletal drug, a gastro-intestinal drug, and anti-allergy drug, an estrogen-containing drug, a drug for the treatment of urinary tract conditions, a drug for the treatment of genital conditions, a drug for the treatment of neurologic conditions, and a drug for the treatment of psychiatric conditions;

b) conducting a randomized, double-blind, cross-over, single patient drug trial of said drug and said placebo in a new patient who is a candidate for treatment with said drug;

c) comparing the information accumulated from the patient population database with the information from the single patient drug trial of said new patient to aid in the interpretation of the results for said new patient;

d) optimizing treatment for said new patient by taking one of the following actions: (i) continuing therapy for said new patient using the same drug and dosage regimen; (ii) changing the dosage regimen of the same drug in order to optimize the dosage regimen for said new patient; or (iii) ceasing to treat said new patient with said drug if the patient is not achieving a desired benefit from treatment with said drug; and e) adding the results from the single patient drug trial of said new patient to the patient population database.

2. The method of claim 1, further comprising assembly of said patient population database by providing to each patient in said patient population a test kit containing a supply of said drug; a supply of said placebo; and a questionnaire designed to elicit from said patient population information concerning the actual usage, safety, efficacy and desirability of said drug.

3. The method of claim 2, further comprising assembly of said information from the individual patient drug trial by providing to said individual patient a test kit containing a supply of said drug; a supply of said placebo; and a questionnaire designed to elicit from said patient information concerning the actual usage, safety, efficacy and desirability of said drug.

4. The method of claim 1, wherein the drug is a drug for treating hyperkinetic behavior.

5. The method of claim 1, wherein the drug is an anti-asthmatic drug.

6. The method of claim 1, wherein the drug is an anti-epileptic drug.

7. The method of claim 1, wherein the drug is a cardiovascular drug.

8. The method of claim 1, wherein the drug is a respiratory drug.

9. The method of claim 1, wherein the drug is an antihypertensive drug.

10. The method of claim 1, wherein the drug is a steroidal anti-inflammatory drug and a non-steroidal anti-inflammatory drug.

11. The method of claim 1, wherein the drug is selected from the group consisting of an opioid analgesic and a non-narcotic analgesic drug.

12. The method of claim 1, wherein the drug is a hematologic drug.

13. The method of claim 1, wherein the drug is a musculoskeletal drug.

14. The method of claim 1, wherein the drug is a gastrointestinal drug.

15. The method of claim 1, wherein the drug is an anti-allergy drug.

16. The method of claim 1, wherein the drug is an anti-depressant drug.

17. The method of claim 1, wherein the drug is an anti-anxiety drug.

18. The method of claim 1, wherein the drug is an anti-psychotic drug.

19. The method of claim 4, wherein the drug is methylphenidate.

20. The method of claim 15, wherein the drug is an antihistamine.

21. The method of claim 7, wherein the drug is verapamil.

22. The method of claim 21, wherein step (d) comprises the step of decreasing the dose of the drug.

23. The method of claim 21, wherein step (d) comprises the step of ceasing to treat the patient.

24. A method of evaluating the therapeutic response of individual human patients to chronic therapy with a drug, comprising:

a) assembling from a plurality of crossover single patient drug trials a patient population database of information concerning the safety, efficacy and desirability of a drug administered according to a randomized, double-blind schedule with a second agent selected from the group consisting of a placebo, a therapeutic alternative for said drug, and a generic equivalent for said drug; said drug being selected from the group consisting of a drug for treating hyperkinetic behavior, an anti-depressant drug, an anti-anxiety drug, an anti-asthmatic drug, an anti-epileptic drug, an anti-psycotic drug, a cardiovascular drug, a respiratory drug, an antihypertensive drug, an anti-diabetic drug, a steroidal anti-inflammatory drug, a non-steroidal anti-inflammatory drug, an opioid analgesic, a non-narcotic analgesic drug, an anti-cancer drug, a hematologic drug, a musculoskeletal drug, a gastro-intestinal drug, a anti-allergy drug, an estrogen-containing drug, a drug for the treatment of urinary tract conditions, a drug for the treatment of genital conditions, a drug for the treatment of neurological conditions, and a drug for the treatment of psychiatric conditions; by providing to each patient in said patient population a test kit containing a supply of said drug; a supply of said second agent; and a questionnaire designed to elicit from said patient population information concerning the actual usage, safety, efficacy and desirability of said drug;

b) conducting in a new patient who is a candidate for treatment with said drug a randomized, double-blind, cross-over, single patient drug trial of said drug and the same second agent administered to the patient population of step (a), by providing to said new patient a test kit containing a supply of said drug; a supply of said second agent; and a questionnaire designed to elicit from said new patient information concerning the actual usage, safety, efficacy and desirability of said drug;

c) comparing the information accumulated from the patient population database with the information from the single patient drug trial of said new patient to aid in the interpretation of the results for said new patient;

d) optimizing treatment for said new patient by taking one of the following actions: (i) continuing therapy for said new patient using the same drug and dosage regimen; (ii) changing the dosage regimen of the same drug in order to optimize the dosage regimen for said new patient; (iii) ceasing to treat said new patient with said drug if said new patient is not achieving a desired benefit from treatment, or (iv) changing said new patient to chronic therapy using a therapeutic alternative or generic equivalent of said drug; and e) adding the results from said single patient drug trial of said new patient to the patient population database.

25. The method of claim 21, wherein step (d) comprises the step of changing the patient, the chronic therapy using a generic equivalent.

26. The method of claim 24, wherein step (d) comprises the step of ceasing to treat the patient and thereby reducing drug cost.

27. The method of claim 24, wherein step (d) comprises the step of changing the individual patient to chronic therapy using a therapeutic alternative and thereby reducing drug cost.

28. The method of claim 24, wherein step (d) comprises the step of changing the individual patient to chronic therapy using a generic equivalent and thereby reducing drug cost.

29. The method of claim 21, wherein the drug is a drug for treating hyperkinetic behavior.

30. The method of claim 21, wherein the drug is an anti-asthmatic drug.

31. The method of claim 21, wherein the drug is an anti-epileptic drug.

32. The method of claim 21, wherein the drug is a cardiovascular drug.

33. The method of claim 21, wherein the drug is a respiratory drug.

34. The method of claim 21, wherein the drug is an antihypertensive drug.

35. The method of claim 21, wherein the drug is a steroidal anti-inflammatory drug and a non-steroidal anti-inflammatory drug.

36. The method of claim 21, wherein the drug is selected from the group consisting of an opioid analgesic and a non-narcotic analgesic drug.

37. The method of claim 21, wherein the drug is a hematologic drug.

38. The method of claim 21, wherein the drug is a musculoskeletal drug.

39. The method of claim 21, wherein the drug is an anti-asthmatic drug.

40. The method of claim 21, wherein the drug is a gastro-intestinal drug.

41. The method of claim 21, wherein the drug is an anti-allergy drug.

42. The method of claim 21, wherein the drug is an anti-depressant drug.

43. The method of claim 21, wherein the drug is an anti-anxiety drug.

44. The method of claim 21, wherein the drug is an anti-psychotic drug.

45. The method of claim 26, wherein the drug is methylphenidate.

46. A method of evaluating the therapeutic response of individual human patients to chronic therapy with a drug, comprising:
   a) assembling from a plurality of crossover single patient drug trials a patient population database of information concerning the safety, efficacy and desirability of a drug administered according to a randomized, double-blind schedule with a placebo, said drug being selected from the group consisting of a drug for treating hyperkinetic behavior, an anti-depressant drug, an anti-anxiety drug, an anti-asthmatic drug, an anti-epileptic drug, an anti-psychotic drug, a cardiovascular drug, a respiratory drug, an antihypertensive drug, an anti-diabetic drug, a steroidal anti-inflammatory drug, a non-steroidal anti-inflammatory drug, an opioid analgesic, a non-narcotic analgesic drug, an anti-cancer drug, a hematologic drug, a musculoskeletal drug, a gastro-intestinal drug, and anti-allergy drug, an estrogen-containing drug, a drug for the treatment of urinary tract conditions, a drug for the treatment of genital conditions, a drug for the treatment of neurologic conditions, and a drug for the treatment of psychiatric conditions;
   b) conducting a randomized, double-blind, cross-over, single patient drug trial of said drug and said placebo in a new patient who is a candidate for treatment with said drug;
   c) comparing the information accumulated from the patient population database with the information from the single patient drug trial of said new patient to aid in the interpretation of the results for said new patient;
   d) optimizing treatment for said new patient by taking one of the following actions: (i) continuing therapy for said new patient using the same drug and dosage regimen; (ii) changing the dosage regimen of the same drug in order to optimize the dosage regimen for said new patient; or (iii) ceasing to treat said new patient with said drug if the patient is not achieving a desired benefit from treatment with said drug.

47. A method of evaluating the therapeutic response of individual human patients to chronic therapy with a drug, comprising:
   a) assembling from a plurality of crossover single patient drug trials a patient population database of information concerning the safety, efficacy and desirability of a drug administered according to a randomized, double-blind schedule with a second agent selected from the group consisting of a placebo, a therapeutic alternative for said drug, and a generic equivalent for said drug; said drug being selected from the group consisting of a drug for treating hyperkinetic behavior, an anti-depressant drug, an anti-anxiety drug, an anti-asthmatic drug, an anti-epileptic drug, an anti-psychotic drug, a cardiovascular drug, a respiratory drug, an antihypertensive drug, an anti-diabetic drug, a steroidal anti-inflammatory drug, a non-steroidal anti-inflammatory drug, an opioid analgesic, a non-narcotic analgesic drug, an anti-cancer drug, a hematologic drug, a musculoskeletal drug, a gastro-intestinal drug, a anti-allergy drug, an estrogen-containing drug, a drug for the treatment of urinary tract conditions, a drug for the treatment of genital conditions, a drug for the treatment of neurologic conditions, and a drug for the treatment of psychiatric conditions; by providing to each patient in said patient population a test kit containing a supply of said drug; a supply of said second agent; and a questionnaire designed to elicit from said patient population information concerning the actual usage, safety, efficacy and desirability of said drug;
   b) conducting in a new patient who is a candidate for treatment with said drug a randomized, double-blind, cross-over, single patient drug trial of said drug and the same second agent administered to the patient population of step (a), by providing to said new patient a test kit containing a supply of said drug; a supply of said second agent; and a questionnaire designed to elicit from said new patient information concerning the actual usage, safety, efficacy and desirability of said drug;
   c) comparing the information accumulated from the patient population database with the information from the single patient drug trial of said new patient to aid in the interpretation of the results for said new patient;
   d) optimizing treatment for said new patient by taking one of the following actions: (i) continuing therapy for said new patient using the same drug and dosage regimen; (ii) changing the dosage regimen of the same drug in order to optimize the dosage regimen for said new patient; (iii) ceasing to treat said new patient with said drug if said new patient is not achieving a desired benefit from treatment, or (iv) changing said new patient to chronic therapy using a therapeutic alternative or generic equivalent of said drug.

* * * * *

UNITED STATES PATENT AND TRADEMARK OFFICE
CERTIFICATE OF CORRECTION

PATENT NO. : 6,242,463 B1
DATED : June 5, 2001
INVENTOR(S) : Donald P. Reitberg

It is certified that error appears in the above-identified patent and that said Letters Patent is hereby corrected as shown below:

Column 18,
Claim 23 should depend from claim 1; claim 25 should depend from claim 24.

Column 19,
Claims 29-44 should depend from claim 24; claim 45 should depend from claim 29.

Column 20,
After claim 47, claims 48-51 should be added as follows:
-- 48. The method of claim 7, wherein the drug is propranolol.
49. The method of claim 41, wherein the drug is an anti-histamine.
50. The method of claim 32, wherein the drug is verapamil.
51. The method of claim 32, wherein the drug is propranolol. --

Signed and Sealed this

Thirtieth Day of July, 2002

Attest:

Attesting Officer

JAMES E. ROGAN
*Director of the United States Patent and Trademark Office*